(12) United States Patent
Glogauer (10) Patent No.: US 7,521,200 B2
(45) Date of Patent: Apr. 21, 2009

(54) METHOD FOR NON-INVASIVE RINSE DIAGNOSIS AND MONITORING OF PERIODONTAL DISEASES USING COLOURIMETRIC REAGENTS

(76) Inventor: Michael Glogauer, 25 Wilmont Court, Hamilton, Ontario (CA) L8S 2T1

( * ) Notice: Subject to any disclaimer, the term of this patent is extended or adjusted under 35 U.S.C. 154(b) by 228 days.

(21) Appl. No.: 11/543,202

(22) Filed: Oct. 5, 2006

(65) Prior Publication Data

US 2008/0085533 A1 Apr. 10, 2008

(51) Int. Cl.
*C12Q 1/26* (2006.01)
(52) U.S. Cl. .......................... 435/25; 435/28
(58) Field of Classification Search .............. 435/25, 435/28
See application file for complete search history.

(56) References Cited

U.S. PATENT DOCUMENTS

| 5,051,358 A | * | 9/1991 | Witt ........................... 435/19 |
| 5,168,044 A | * | 12/1992 | Joyce et al. ................ 435/7.24 |
| 2005/0032126 A1 | * | 2/2005 | Coombs et al. ............. 435/7.2 |
| 2005/0220712 A1 | * | 10/2005 | Wright et al. ................ 424/9.6 |

FOREIGN PATENT DOCUMENTS

| JP | 2008 005838 | * | 5/2007 |
| SU | 1366947 A | * | 1/1988 |

OTHER PUBLICATIONS

Bender J. et al. Novel Rinse Assay for the Quantification of Oral Neutrophils and the Monitoring of Chronic Periodontal Disease. J Periodontal Research 41:214-220, 2006.*
Hanioka T. et al. Relationship Between Periodontal Disease Status and Combination of Biochemical Assays of Gingival Crevicular Fluid. J Peridontal Research 40:331-338, 2005.*
Sakamoto W. et al. A Novel Assay System for Myeloperoxidase Activity in Whole Saliva. Clinical Biochemistry 41:584-590, 2008.*
J.S. Bender, H. Thang, M. Glogauer "Novel rinse assay for the quantification of oral neutrophils and the monitoring of chronic periodontal disease", Periodontal REs. 2006; 41:214-220: circa Jan. 2006.

* cited by examiner

*Primary Examiner*—Ralph Gitomer (57) ABSTRACT

An assay test kit is used in a mouth rinse sample collection procedure involving collecting a mouth rinse sample from a patient. A neutrophil reactant diagnostic reagent is delivered to the rinse sample immediately after collection. Diagnostic reagents containing diammonium salts that are reactive with neutrophil enzymes are added to the sample to produce visually discernable color change in the solution after a selected period of time. Most preferably, the reagents are selected to produce a color change after a period of time. The reaction is then measured by comparing the resulting sample color change by eye or mechanically to a standardized color chart/swatch that correlates with predetermined neutrophil concentrations and/or periodontal disease levels.

18 Claims, 9 Drawing Sheets

*Figure 1.* Cropping of the samples' colors.

FIGURE 3

Analysis of the luminosities of two controls.

The dependence of reflectance on the amount of neutrophils.

METHOD FOR NON-INVASIVE RINSE DIAGNOSIS AND MONITORING OF PERIODONTAL DISEASES USING COLOURIMETRIC REAGENTS

SCOPE OF THE INVENTION

The present invention relates to a quick, easy-to-use, non-invasive diagnostic test for diagnosing and/or monitoring the severity of periodontal diseases in human patients.

BACKGROUND OF THE INVENTION

Screening for periodontal diseases has heretofore required regular visits to the dentist in order for a regular examination to be carried out. Periodontal diseases are inflammatory conditions that result in loss of the bone, gingiva and ligament that support the teeth. The destruction of the tooth supporting tissues (periodontium) occurs as a result of collateral damage caused by enzymes released by specialized white blood cells called neutrophils as they attempt to contain the bacterial infection. Periodontal diseases are one of the most prevalent diseases occurring in man, with between 70 and 90% of the population experiencing this disease during their lifetime.

Typically, diagnosis of the severity of periodontal diseases are determined by periodic professional dental examination of the amount of lost bone, ligament and gingival tissues. This examination requires the insertion of a thin metal probe under the gum tissues surrounding the teeth. The depth to which to probe extends is noted indicating the degree of "detachment" and loss of the supporting tissues around the teeth. A key measure is the degree of bleeding that occurs following probe insertion which indicates the degree of inflammation and ongoing disease. This bleeding provides a crude quantitative measure of disease level. Many studies have shown that the degree of bleeding is the most accurate predictor of future periodontal tissue loss around a given tooth.

There are also biochemical tests that have been developed to identify enzymes that are released by cells of the periodontium and the immune system into the oral cavity. However these tests require specialized equipment and training to carry out.

Since periodontal diseases usually do not cause pain, patients will often not be aware that there is any active disease occurring in their mouths. Some may notice occasional bleeding when they brush their teeth but most choose to ignore this as the bleeding is often transient in nature. Earlier studies have correlated the presence of neutrophils entering into the mouth through the gingival crevice surrounding the teeth in the crevicular fluid as a possible measure of oral inflammation. Currently, microscopes are sold to dentists to enable them to visually count or quantify neutrophils taken from samples around teeth.

SUMMARY OF THE INVENTION

A significant problem in society is rapidly and inexpensively identifying geriatric and institutionalized patients in need of dental care. This is a significant healthcare issue as recent studies have identified significant links between periodontal diseases and 1) cardiovascular diseases including heart attacks and strokes, 2) diabetes and 3) aspiration pneumonia. Being able to identify periodontal diseases in institutionalized elderly patients using a rapid non-invasive test that can be administered by non-specialized staff has the potential to have a significant impact on this population and the healthcare system.

The inventor has proposed an earlier method of quantifying oral mucosal neutrophils to detect a likelihood of periodontal diseases. In particular, neutrophils are collected with an oral saline rinse, stained with acridine orange and counted using fluorescence microscopy. In the inventor's earlier studies comparing a control group of healthy patients, and a group of individuals with moderate and severe chronic periodontal diseases, oral neutrophil counts were compared together with the degree of periodontal disease and oral inflammation. The inventor has appreciated that oral neutrophil counts may be used to provide an excellent measure of not only identifying patients with periodontal disease in need of treatment, but also as a means of monitoring the elimination of infection and the effectiveness of any remedial treatments.

It is clear based on the available knowledge relating to neutrophil kinetics in the human organism, that access to a non-invasive, simple, quick colourimetric, test capable of being self administered by outpatients and by non-skilled personnel will readily benefit patients by helping identify those in need of treatment. The inventor's conclusions have led to an investigation into the development of a rapid test based on a colourimetric assay employing a neutrophil-specific enzymatic reaction to assess their presence of periodontal diseases.

Accordingly, an object of the invention is to provide an assay test for assessing the presence of periodontal disease which is simple enough to enable non-specialized health care workers or even patients to self-administer the test, eliminating the need for dentist visits and/or time-consuming microscopic counting of neutrophils.

A further object is to provide a simplified kit for the identification of periodontal diseases which uses a colourimetric change reaction in the rinse solution, such as a colour change, a colour intensity change, or other suitable visual indicator. The visual indicator may then be manually or electronically compared to a predetermined standard colour or colour chart relating the solution colour to the number of neutrophils present in the sample and the level of oral inflammation present in the patient's mouth.

In another aspect the applicant has proposed a rapid non-invasive diagnostic test to quantify neutrophils and/or oral inflammation in the mouth.

In one possible embodiment, a 15 to 60 second and more preferably a 30 second mouth rinse sample is obtained. A diagnostic reagent is added to the sample which is colour reactive with neutrophils. A resulting colour change is observed preferably in as little as 5 to 10 seconds, and more preferably in about 60 seconds which indicates a number of white blood cells present in the rinse based on a standardized scale. The detected oral neutrophil levels may be then used to correlate with the severity of the periodontal disease/oral inflammation present in the patient.

In a more preferable assay, the patient may first pre-rinse with a cleansing solution such as water or an alcohol or antiseptic based solution, to effectively sterilize the oral cavity prior to obtaining the mouth rinse sample.

In an alternate embodiment, the present invention employs an assay test using a modified mouth rinse sample collection procedure. The test involves collecting a mouth rinse sample from a patient. A diagnostic reagent that specifically reacts with white blood cell specific enzymes and results in a colour change n the rinse solution is then delivered to the rinse sample immediately after sample collection. Suitable diagnostic reagents contain a diammonium salt that are reactive with neutrophil enzymes which create a visually discernable colour change in the solution after a selected period of time. Most preferably, the reagents are selected to produce a colour change in between about 3 and 120 seconds, and most preferably about 60 seconds. At 60 seconds a detergent is added to stop and fix the colour reaction. The intensity of the colour reaction may be measured by reflectance or absorbance, or due to the large colour range by eye when comparing the sample to a standardized colour chart/swatch that correlates with predetermined neutrophil concentrations and/or periodontal disease levels.

The correlation of the colour changes and/or changing colour intensity are compared to standards that relate observed colour intensity levels to neutrophils numbers present in samples with varying oral/periodontal disease levels. The colour chart correlations may be supplied on printed labels, card and or instruction materials as part of an assay kit supplied to dentists, or patients/health care workers to facilitate the self-administration of the test, and enhance understanding of the test results.

Accordingly, in one aspect the present invention resides in an in vitro method for identifying the presence of periodontal diseases in a human patient's mouth comprising the steps of:
obtaining an oral rinse sample from said patient's mouth;
adding a colourimetric reagent to the rinse sample;
admixing the oral rinse sample and the colourimetric reagent to form a mixed solution; and
comparing a colour intensity or shade of the mixed solution with at least one predetermined colour standard representative of selected number of human neutrophils in the mixed solution.

In another aspect, the present invention resides in an assay test for the in vitro identification of the presence of periodontal diseases in a human patient, said assay test including;
a volume of sampling solution for use in obtaining an oral rinse sample;
a receptacle for obtaining a volume of said oral rinse sample expectorated by said patent;
a colourimetric reagent for addition to the rinse sample, the diagnostic reagent comprises a lysic agent selected to lyse neutrophils in said oral rinse sample, a buffer for regulating the pH of the lysed solution and a neutrophil reactant salt; and
at least one predetermined colour standards representative of selected numbers of human neutrophils in the solution.

In yet a further aspect, the present invention resides in a method for identifying the presence of periodontal diseases in a human patient's mouth comprising the steps of (a) obtaining an oral rinse sample from said patient's mouth by swishing a measured quantity of a saline/bicarbonate buffer mouthwash around said mouth for a timed interval of about 30 second; (b) adding a measured quantity of a diagnostic colourimetric reagent to the rinse sample; (c) agitating and/or inverting the solution at least once to mix; (d) comparing the colour and/or intensity of the colour of the rinse sample with a chart of predetermined colour standards that correlate with a predetermined number of human neutrophils in the sample.

BRIEF DESCRIPTION OF THE DRAWINGS

Reference may now be had to the following detailed description, taken together with the accompanying drawings in which.

DETAILED DESCRIPTION OF THE INVENTION

The present invention resides in a method of quantifying neutrophil levels in the oral cavity of a patient as an accurate indicator of the existence and/or severity of a periodontal disease in a patient's mouth, and consequently of the need for dental treatment.

In a first embodiment, the present invention provides a method and rinse for use in determining neutrophil concentrations in a patient's mouth as a means of identifying the presence of periodontal disease. Preferably, the patient first pre-rinses his or her mouth with a cleansing solution to clear debris and any excess neutrophils which may be residually present. Suitable cleansing solutions would include tap water, distilled or purified water, as well as alcohol and/or antiseptic based mouthwashes. Most preferably, the patient pre-rinses with between about 3 and 20 ml, and preferably about 5 ml of a sterile saline mouthwash (0.9%) solution for 10 to 30 seconds to effectively clear debris.

Within 10 minutes, and most preferably substantially immediately following pre-rinsing, the patient undertakes a second oral rinse to obtain an assay sample. The second oral rinse involves rinsing between about 3 and 20 ml., and preferably about 5 ml of a sterile saline mouthwash (0.9%) for 30 seconds.

Figure 1:
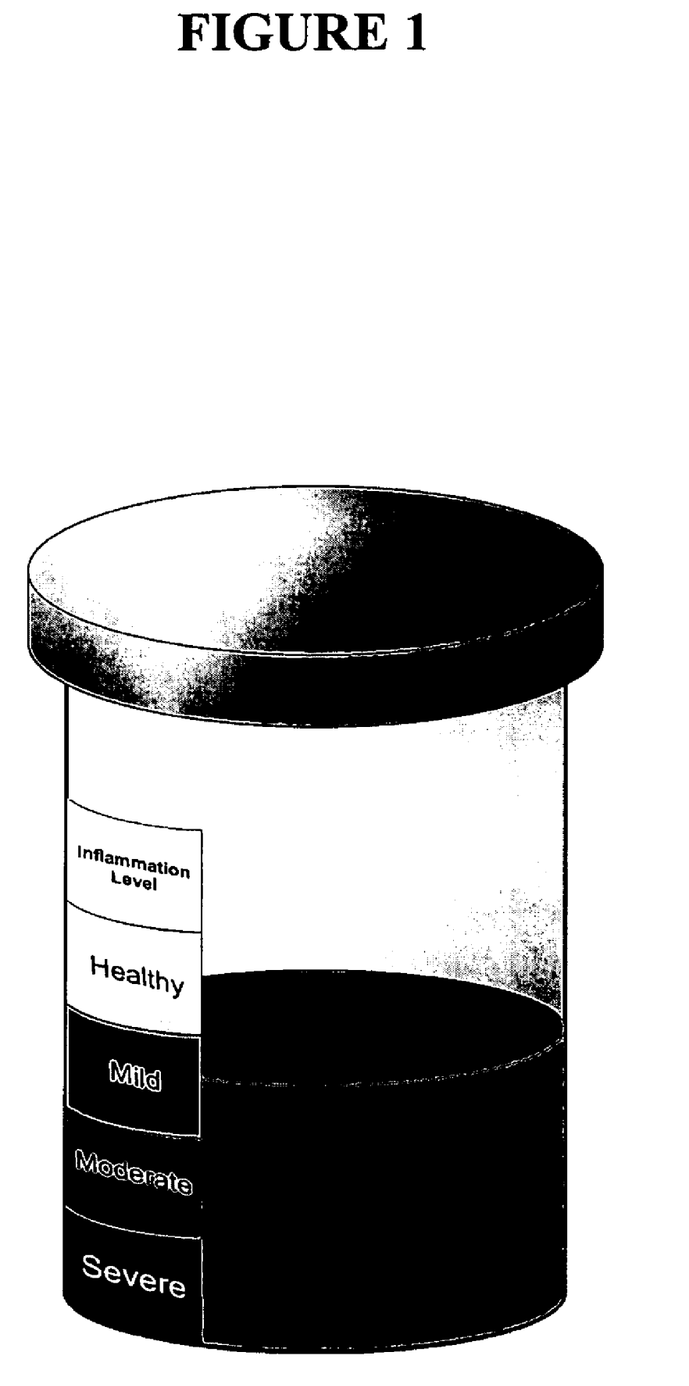
FIG. 1 shows schematically an oral rinse sample container having affixed thereto a colour intensity chart correlating the average neutrophil levels in patients with healthy mouths and those with moderate and severe periodontal disease.

Following the collection of the assay sample, a colourimetric indicator solution is added to the rinse after collection in a container/mixing tube. Suitable indicator solutions include diammonium salts in preferred concentrations of between about 200 mg to 500 mg/100 ml together with a lysic agent such as 0.5 to 5% anionic detergent selected to lyse neutrophils in the assay sample. Optionally, hydrogen peroxide 100 to 500 ul/100 ml and/or a buffer may also be provided for regulating the pH of the lysed solution. Suitable buffers would include citrate based buffers. The sample mixture is agitated and/or inverted at least once, and preferably twice to thoroughly mix whereby the reaction between the salt and the neutrophils produces a resultant change in colour and/or intensity. Sodium dodecyl sulphate can be added after reaction (approximately 60 seconds) to allow for stabilization of the solution colour. The intensity of the resultant sample colour is thereafter compared to the provided colour scale 34, as for example, is shown in FIG. 1.

The colourimetric indicator most preferably contains: a) an anionic detergent selected to lyse the cells and expose the characteristic human neutrophil enzyme, such as those sold as Triton X-100™ or NP-40™); b) a buffer to correct the pH of the lysed cell solution (ie. Sodium citrate); and c) a neutrophil reactant salt which acts as a reagent that reacts with myeloperoxidase, an enzyme found in neutrophils, to form a green-blue colour (2,2'-Azino-bis(3-ethylbenzo-thiazoline-6-sulfonic acid).

(ABTS) salt is most preferred as it serves as a substrate for myeloperoxidase, and one of the reaction's products is chromogenic, producing a light blue-green colour which is visible to the human eye. Other possible examples of salts could, however, also be used including, without restriction: 2,2'-azino-bis(3-ethylbenzthiazoline-6-sulfonic acid)diammonium salt; 2,7-diaminofluorene, 3,3',5,5'-tetramethylbenzidine and its dihydrochloride salt; 5-aminosalicylic acid, o-phenylenediamine and its dihydrochloride salt; 5-amino-2, 3-dihydro-1,4-phthalazinedione, 3-amino-9-ethylcarbazole, 4-chloro-1-naphthol, 3,3'-diaminobenzidine, o-dianisidine and its dihydrochloride salt, guaiacol and pyrogallol.

The present invention satisfies the need to provide a simple test for oral neutrophils to provide an indication of periodontal disease, and which can be used outside as well as inside a hospital/clinical setting. The test can also be administered by the patient him/herself, by patient, family members, non-specialist primary care physicians, dental office hygienist assistants, and/or private duty nurses caring for patients in the home.

Furthermore, this test can be used to easily monitor and/or map any subsequent changes of a patient's oral health status, to enable more rapid and frequent screening and diagnosis.

The assay test employs an indicator having a novel composition in solid or solution form. The kit includes a container 12 (FIG. 7) which may optionally include two compartments which are used to maintain one or more components of the solution and/or reagent discrete and apart prior to use. As will be described, in one preferred construction, ABTS is maintained in a solid form separately from the remaining components of the indication which may be solid, but more preferably which are housed in liquid form (ie. detergent, citrate buffer, and hydrogen peroxide). Immediately prior to use the powder is mixed with the liquid solution to form an active colourmetric indicator.

a) Determination of Colour Scale (Independent of a Patient's Age, Sex and Systemic Health Status)

To produce the colour scale 34, the inventor has first developed a set protocol. This protocol set rules for several parameters, including the conditions for taking the photographs of the oral rinse samples. Lighting conditions, background, aperture size and exposure had to be standardized in order to obtain consistent results. Furthermore, the quantities of neutrophils for the samples were, after experimentation, set to 1, 3, 6 and 12 million per sample. These were selected to correspond to a realistic range of neutrophil quantities in patients with various levels of periodontal disease severity (see FIG. 1).

After the establishment of this protocol, neutrophils were isolated from human blood and used to obtain multiple samples and photographed using digital photography.

Figure 2:
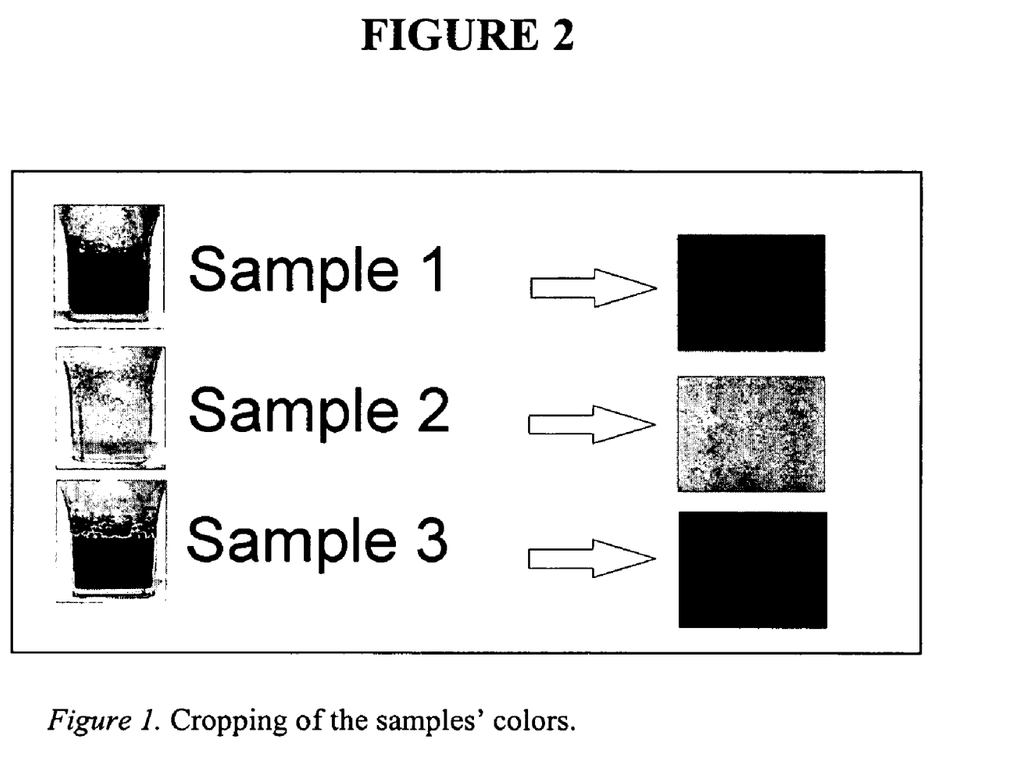
FIG. 2 shows a comparison of resultant sample colours utilizing an ABTS diammonium salt as a neutrophil reactive reagent with predetermined colour charts in accordance with the preferred embodiment of the invention.

The digital photographs were then cropped as for example shown and analyzed using image analysis software. The resultant luminosity histograms were compared for the different samples to further establish the consistency of the method. As can be seen from FIG. 2, successive samples with the same approximate number of neutrophils have the same dominant color. In other words, FIG. 2 shows peaks, from left to right, which symbolize samples with decreasing concentrations of neutrophils. The lighter blue colors have higher luminosity values, and the peaks at 255 represent white—total absence of neutrophils.

Figure 3:
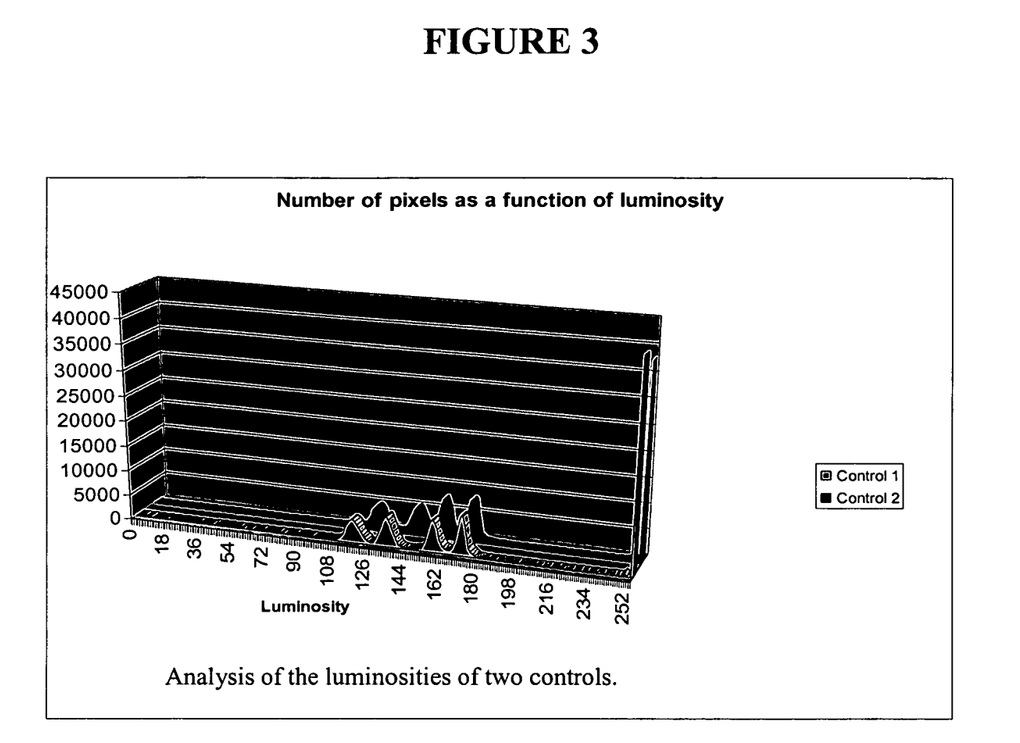
FIG. 3 shows graphically luminosity histograms of control samples showing the luminosity of differing neutrophil levels.

From the test criteria, the inventor has proposed the production of a single color scale shown in FIG. 3.

b) Quantitative Correlation

To obtain a quantitative relationship between the color of the oral rinse and the quantity of neutrophils, a calibration curve was constructed, with the reflectance percentage as a function of the quantity of neutrophils. To accomplish the above, the color range of neutrophil dilutions was compared to the reflectance values.

Figure 4:
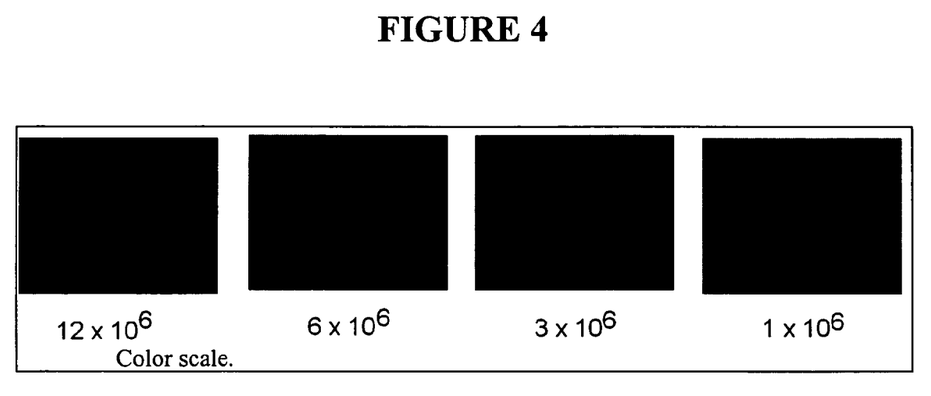
FIG. 4 shows a sample predetermined colour scale which is representative of neutrophil levels in the patient, used to provide an indication of a likelihood of periodontal disease/oral infections in a patient.

The equation of the standard curve as shown in FIG. 4 is calculated by equation 4.1 as follows:

$$y = -0.0815 Ln(x) + 0.6869 \qquad (4.1)$$

Figure 5:
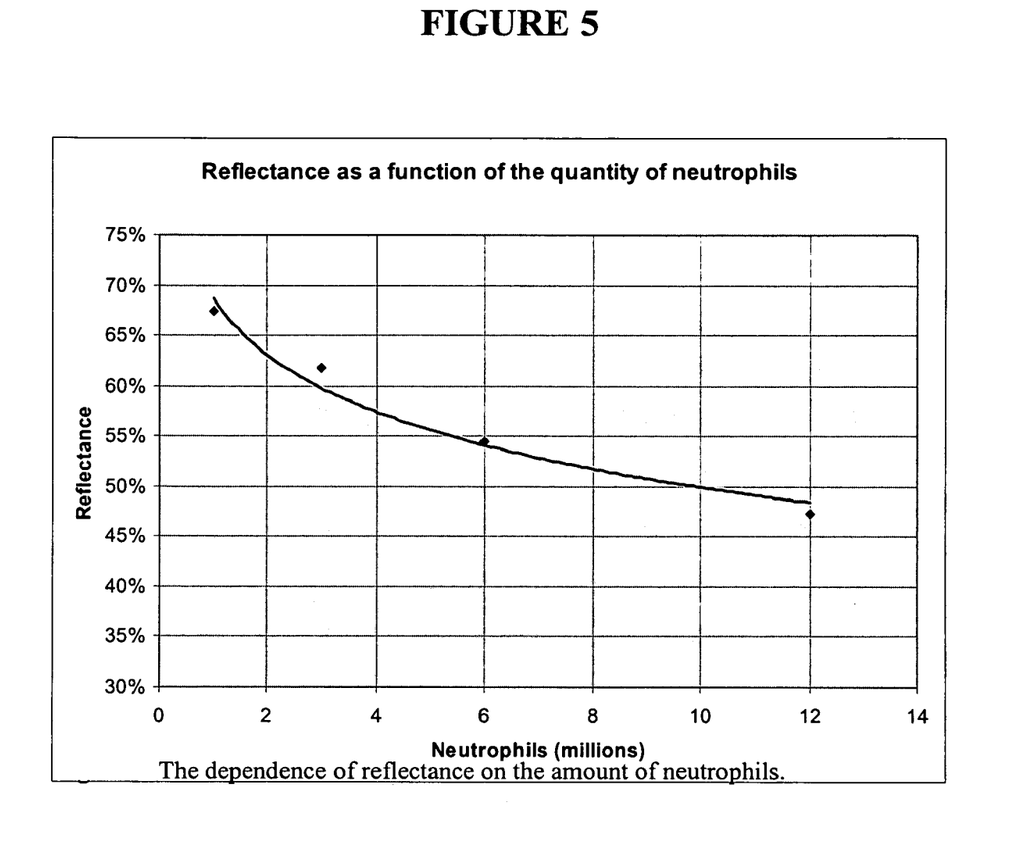
FIG. 5 illustrates the colour/neutrophil concentration relationship using an ABTS diammonium salt as a reagent.
Figure 6:
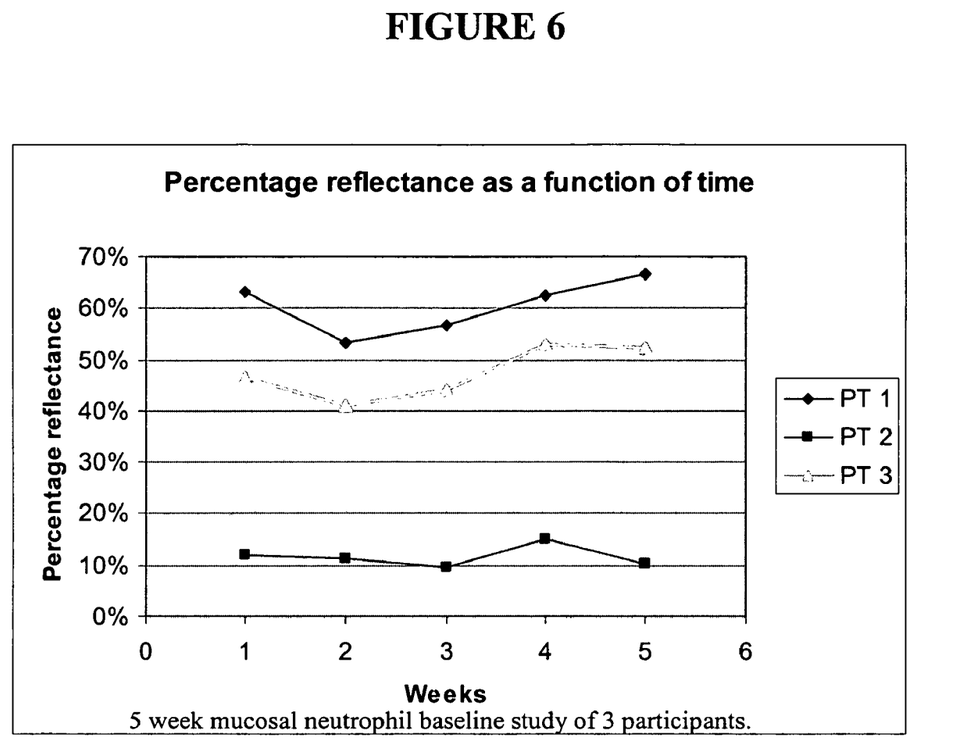
FIG. 6 illustrates graphically mucosal neutrophil concentrations in clinical subjects over time (from day to day)

In equation (4.1), "y" stands for the percentage reflectance of the solution and the "x" stands for the quantity of neutrophils in the sample. The symbol "Ln(x)" as used in the equation represents the natural logarithm of "x"-logarithm with base e. Although the relationship between the concentration of neutrophils and the reflectance is an inverse one, the most accurate representation was found to be logarithmic. This was so due to the fact that in a real experimental situation, the reflectance would never be 100%, but rather would approach the 100% value asymptotically. The reflectance can be read in a spectrometer to obtain numeric values. This would facilitate research but would have minimal benefit in a purely clinical setting.

c) Establishment of a Reproducibility of Day to Day Measurements in a Given Patient Using the sample collection method described earlier, the measurement methodology established in Example 1, and the ABTS solution, the day to day reproducibility of an individuals oral mucosal neutrophil levels was established. In the control population, the mouthwash samples were obtained at exactly the same time of day on five separate days over a time period spanning four weeks. Each collection was evenly spaced one week after the previous collection. FIG. 5 below shows the measured reflectance results for each test day for the control population.

The individual lines in the study (FIG. 5) show a high degree of reproducibility in mucosal neutrophil concentration for each individual.

d) Clinical Example

To provide an example of the in depth luminosity analysis, the previously established methodology was employed to analyze the oral neutrophil levels of 4 patients. After photographing their oral rinses, the data was analyzed to produce FIG. 9.

Figure 9:
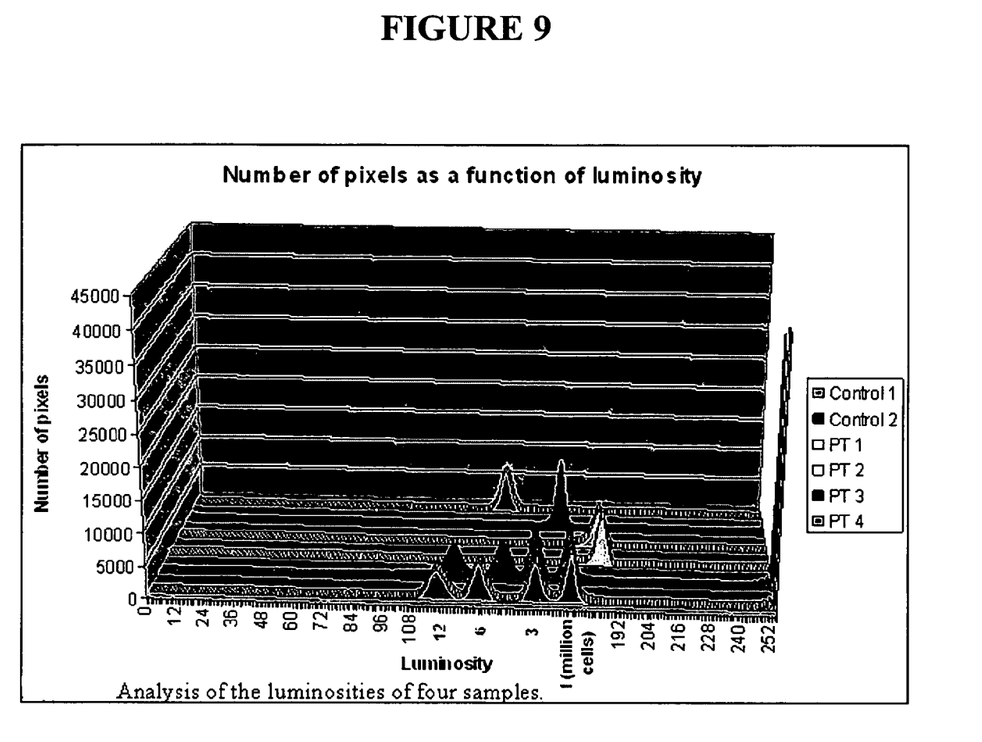
FIG. 9 illustrates graphically the luminosity of the neutrophil levels between control patients and those exhibiting periodontal disease.

As can be seen from FIG. 9, participants 1 and 2 (PT 1 and PT 2) have fewer than 1 million neutrophils in their rinses, indicating a healthy oral cavity. This was subsequently confirmed by a dental examination. The oral rinse supplied by Participant 3 has fewer than 3 million neutrophils in the sample rinse. This neutrophil activity level also suggested a healthy individual, and minor gingivitis was confirmed in the patient by a dental examination. On the other hand, the oral rinse provided by participant 4 revealed elevated levels of neutrophil of a somewhere in the range between 6 and 12 million in each sample rinse. These levels suggested that the patient has periodontal disease or oral infection and should be referred to a dental practitioner for further treatment. Subsequent dental examination confirmed active periodontal infections in participant 4, resulting in loose teeth and alveolar bone loss.

Although digital analysis of the luminosity of the sample was undertaken for the clinical example study, it is to be appreciated that this is not, in fact, essential. In a simplified test, it is possible to simply compare the rinse colour or colour intensity to provide standardized color swatch with the unaided eye, to arrive at a diagnosis in a similar manner.

Overall, the studies support the claim that a patient's oral neutrophil levels tend to maintain at a stable level, unless the state of the patient's oral health changes. Furthermore, the studies show that a calibration curve can be constructed, quantitatively tying color indicators, such as colour shade and/or colour intensity, to a patient's oral mucosal neutrophil concentration.

e) Assay Kit for Home Use

Figure 7:
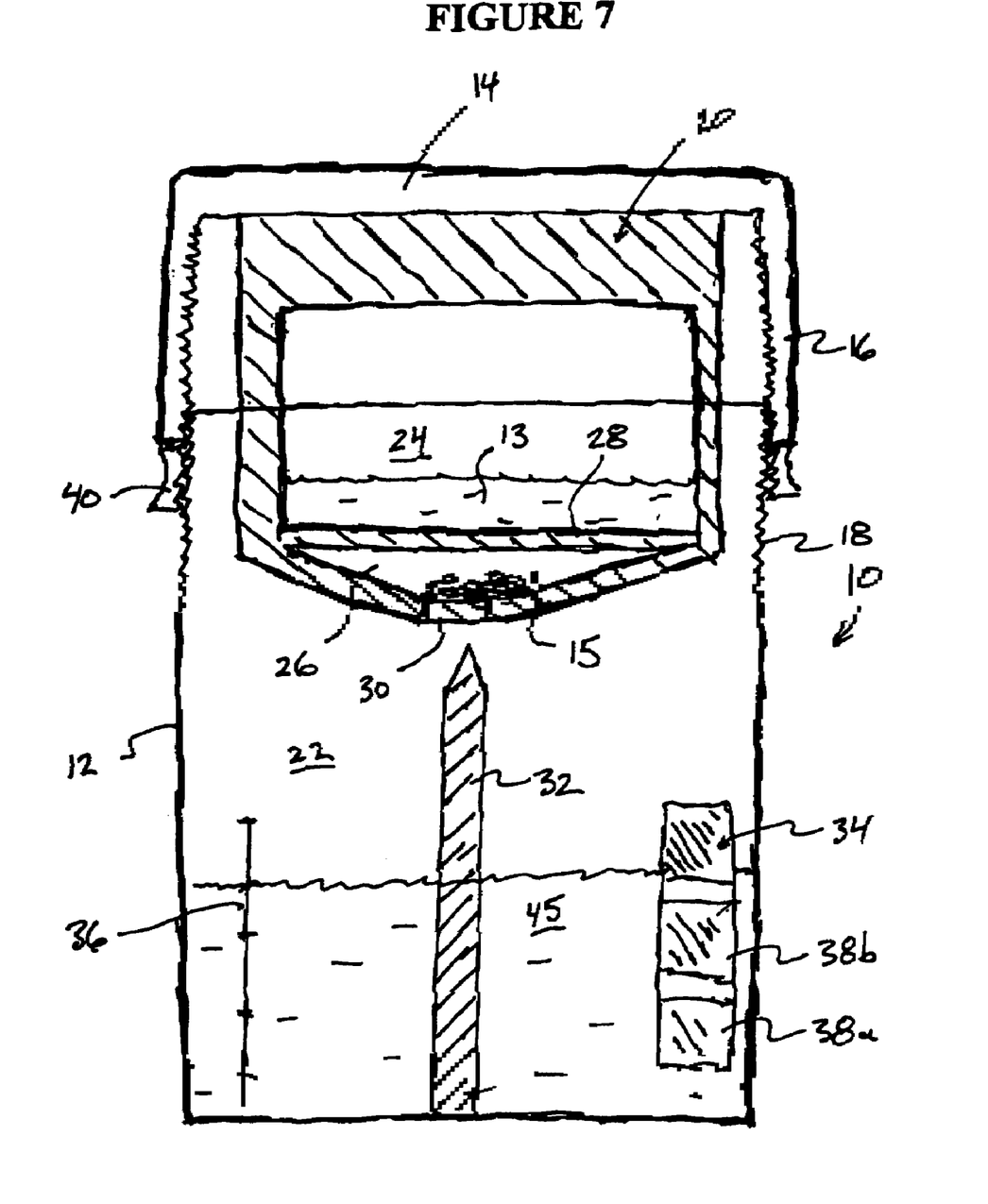
FIG. 7 illustrates schematically an assay kit for use in the home assay of neutrophil levels in the diagnosis of periodontal disease, in accordance with a preferred embodiment of the invention.
Figure 8:
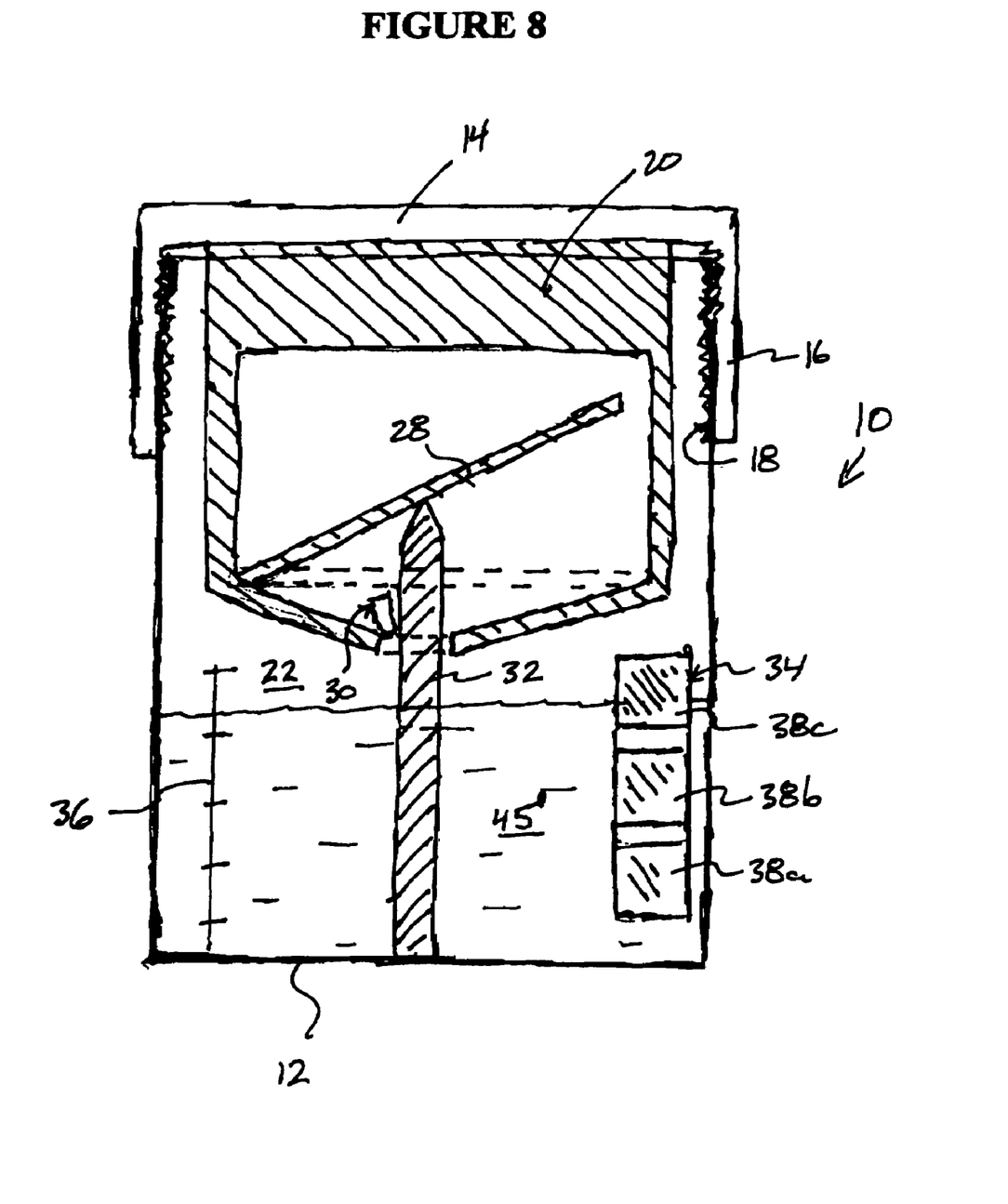
FIG. 8 illustrates the assay kit of FIG. 8 when activated in use.

Reference may be had to FIGS. 7 and 8 which illustrate schematically a single use in-home assay kit 10 for use in the diagnosis and/or monitoring of periodontal diseases.

The single assay test kit 10 is used with a single serving colourimetric indicator solution is prepared which includes as a diamonium salt, 2,2'-Azino-bis(3-ethylbenzo-thiazoline-6-sulfonic acid) (ABTS) diammonium salt; in a concentration of 3.2 to 3.6 mg/ml, a detergent (1% Triton X-100), 30% hydrogen peroxide (200 ul/100 ml) and sodium citrate buffer (380 mM) in a recipe as follows:

Single Serving Recipe 188.7 μL-10% Triton (1.88%)

377.3 μL-1 M Citrate Buffer (377 mM)

5 μL H2O2

431.4 μL H2O 3.6 mg-ABTS powder

... as a liquid component 13

3.6 mg-ABTS powder

... as a solid component 15

The assay kit 10 includes a transparent and most preferably clear plastic container 12 and a cap member 14. As shown best in FIG. 2, the cap member 14 is provided with an internally threaded peripheral flange 16 which is configured for threaded engagement with an externally threaded upper edge portion 18 of the container 12. As shown best in FIG. 7, a two-part chamber 20 is mounted to the underside of the cap member 14. The chamber 20 is sized and positioned for partial insertion into the container interior 22 as the cap member 14 is secured in place. The chamber 20 is used to house the colourmetric indicator solution used in assaying neutrophil concentrations in two-part form. The chamber 20 includes an uppermost liquid cavity 24 which houses the liquid component 13 and a lowermost solid reagent cavity 26 which houses the solid component 15. As will be described, prior to the use of the assay kit 10, the solid cavity 26 is maintained separate and discrete from the liquid cavity 24 by a detachable seal member 28 which delineates the bottom of the liquid cavity 24 from the top of the solid cavity 26. The bottom of the solid cavity 26 is furthermore initially sealed by a detachable septum 30.

FIG. 7 shows best the container 12 as including a bayonet member 32. The bayonet member 32 is secured to the bottom of the container 12 and projects axially upwardly therefrom so as to be selectively engageable with both the septum 30 and seal member 28 as the cap member 14 is tightened downwardly onto the container 12.

Optionally, a colour scale 34 and graduation markings 36 may be provided along the outside of the container 12. The colour scale 34 is provided with a number of pre-printed colour slides 38a,38b,38c which represent resulting colours produced by the reaction of predetermined threshold members of neutrophils with a colourmetric indicator solution formed from mixing the dry solid component 15 contained in the solid cavity 26 with the liquid component 13 contained in the liquid cavity 24. As shown best in FIG. 7, when initially purchased, the container 12 of the assay kit 10 is precharged with a preselected volume and preferably approximately 5 ml of a sterile saline mouthwash solution (0.9% salt). The two-part chamber 20 of the cap member 14 is furthermore preloaded with the indicator solution in two-part form and including 3.2-3.6 glml of ABTS powder as the solid reactive component 15. The liquid cavity 24 is similarly preloaded with a liquid solution of Triton X-100 as a detergent, hydrogen peroxide and sodium citrate buffer as the liquid component 13. A sodium dodecyl sulphate powder/tablet (between 1 and 50 mg but preferably 25 mg) is provided as an optional stop reagent to be added after 60 seconds of colour reaction to stabilize the colour change if the rinse is to be preserved/colour reaction needs to be saved for any reason. At the time of initial purchase of the assay kit 10, the cap member 14 is secured to the container 12 so that only the lowermost peripheral threaded edge of the flange 16 engages the uppermost portion of the externally threaded edge 18 of the container. Optionally, a detachable locking ring 40 (FIG. 7) may be provided to prevent unintentional tightening of the cap member 14 onto the container.

In use of the assay kit 10, the patient initially pre-rinses with either tap water, or more preferably, distilled water for a period of about 30 to 60 seconds. Following a predetermined period of time which preferably is selected at between about 5 seconds and 5 minutes, the user activates the assay kit 10 by first fully detaching the cap member 14 so as to break and remove the locking ring 40. With the cap member 14 removed, the user then rinses with the sterile saline mouthwash solution 45 for a period of approximately 10 to 30 seconds. Following rinsing, the solution is expectorated back into the container 12 as an oral rinse solution 45' ensuring that a desired volume of fluid is achieved according to the graduated marking 36. The cap member 14 is then immediately repositioned onto the container 12 and fully tightened by the engagement of the flange 16 with the threaded edge 18 to the position shown in FIG. 8. As the cap member 14 is moved further onto the container 12, the bayonet member 32 is moved initially into bearing contact with the septum 30. Initially, engagement with the bayonet member 32 results in the detachment of the septum 30 allowing the solid component 15 to move under gravity into the oral rinse solution 45'. Continued tightening of the cap member 14 results in the bayonet member 32 next engaging and detaching the seal member 28. The detachment of the seal member 28 enables liquid component 13 to flow downwardly first into and through the solid cavity 26 and outwardly through the bottom therefrom into the container interior 12 where it admixes with the solution 45'. The flow of the liquid component 13' into the solid cavity 26 advantageously flushes any residual solid component 15 from the chamber 20 into the container interior 22.

The container 12 is thereafter shaken, agitated or inverted to allow full mixing of the colourmetric reagents and reaction with any neutrophils from the patient's mouth which are present in the oral rinse solution 45'. Following reaction with the reagent for a period of time preferably selected at between 5 and 60 seconds, the resulting solution will change colour having regard to the neutrophil concentration. The user thereafter may visually compare the colour of the admixed solution with the appropriate colour panel 38a,38b,38c of the colour scale 34 to provide a visual indication of the likely presence and/or severity of periodontal disease.

Although FIGS. 7 and 8 illustrate an assay kit 10 having a two-part chamber containing cap member 14, the invention is not so limited. It is to be appreciated that assay kits could equally be provided in which the colourmetric indicators are provided in separate containers for subsequent decantation into the container 12. Optionally, the kit 10 may be provided without a predetermined volume of sterile saline mouthwash solution or with separate containers containing both volumes of pre-rinse solutions and sampling solutions.

The colourimetric method and assay kit of the present invention shows outstanding sensitivity, precision and accuracy relative to standard methods used to diagnose periodontal diseases. Furthermore, the assay kit may be self-administered and is more rapid than current microscope based methods used for counting oral neutrophils.

Although the detailed description describes and illustrates preferred embodiments, the invention is not so limited. Many modifications and variations will now occur to persons skilled in the art. For a definition of the invention reference may be had to the appended claims.

I claim:

1. An in vitro method for identifying the presence of periodontal diseases in a human patient's mouth comprising the steps of:
   obtaining an oral rinse sample from said patient's mouth;
   adding a colourimetric reagent to the rinse sample;
   admixing the oral rinse sample and the colourimetric reagent to form a mixed solution; and
   comparing a colour intensity or shade of the mixed solution with at least one predetermined colour standard representative of a selected number of human neutrophils in the mixed solution indicative a presence or absence of periodontal disease.

2. The method as claimed in claim 1 wherein immediately prior to the step of obtaining the oral rinse sample, pre-rinsing said patient's mouth to remove debris, and wherein at least one of said predetermined colour standard is representative of at least $5 \times 10^6$ neutrophils in the mixed solution.

3. The method as claimed in claim 2 wherein the colourimetric reagent comprises a salt selected from the group consisting of-2,2'-azinoe-bis(3-ethylbenzo-thiazoline-6-sulfoflic acid) diammonium salt; 2,2'-azino-bis(3-ethylbenzthiazoline-6-sulfonic acid) diammonium salt; 2,7-diaminofluorene; 3,3',5,5'-tetramethylbenzidine and its dihydrochloride salt; 5-aminosalicylic acid; o-phenylenediamine and its dihydrochioride salt; 5-amino-2,3-dihydro-1,4-pbthalazinedione; 3-amino-9-ethylcarbazole; 4-chloro-1-naphthol; 3,3'-diaminobenzidine; o-diamsidine and its dihydrochioride salt; guaiacol; and pyrogallol.

4. The method as claimed in claim 1 wherein said rinse sample is obtained by swishing and expectorating a measured quantity of mouth rinse solution after a predetermined period of time.

5. The method as claimed in claim 4 wherein said predetermined period of time is selected at between 15 and 120 seconds.

6. The method as claimed in claim 5 wherein said predetermined period of time is selected at between 20 and 40 seconds.

7. The method as claimed in claim 4 wherein said mouth rinse solution is selected from the group consisting of a sterile saline mouthwash solution and a saline/bicarbonate buffer solution.

8. The method as claimed in claim 7 wherein the colourimeteric reagent further comprises a lysing agent selected to lyse neutrophils in said rinse sample and a buffer for regulating a pH of the lysed solution.

9. The method as claimed in claim 8 wherein said lysing agent comprises an anionic detergent.

10. The method as claimed in claim 9 wherein said colourimetric reagent further comprises hydrogen peroxide and a neutrophil-reactant salt comprising an ABTS (2,2'-Azino-bis (3-ethylbenzo-thiazoline-6-sulfonic acid) diammonium salt in an effective amount selected to react with said neutrophils so as to form a colour indicator.

11. The method as claimed in claim 10 wherein said colour indicator comprises a green-blue colour.

12. The method as claimed in claim 10 wherein said colour intensity of the mixed solution is compared with a plurality of predetermined colour intensity standards, at least a first one of said colour intensity standard being representative of a concentrations of at least 5 million human neutrophils in the mouth rinse solution; and a second one of said colour intensity standards being representative of a concentration of at least 10 million neutrophils in the mouth rinse solution.

13. The method as claimed in claim 1 wherein said colourmetric reagent further comprises hydrogen peroxide and a neutrophil-reactant salt comprising an ABTS (2,2'-Azino-bis (3-ethylbenzo-thiazoline-6-diammonium salt in an effective amount selected to react with said neutrophils so as to form a colour indicator.

14. A method for identifying the presence of periodontal diseases in a human patient's mouth comprising the steps of (a) obtaining an oral rinse sample from said patient's mouth by swishing a measured quantity of a saline/bicarbonate buffer mouthwash around said mouth for a timed interval of about 30 seconds; (b) adding a measured quantity of a diagnostic colourimetric reagent to the rinse sample; (c) agitating and/or inverting the rinse sample at least once to mix; (d) comparing the colour and/or intensity of the colour of the rinse sample with a chart of predetermined colour standards that correlate with a predetermined number of human neutrophils in the sample indicative of the presence or absence of periodontal disease.

15. The method according to claim 14 wherein the diagnostic reagent is a combination of an anionic detergent to lyse the cells, a buffer selected to optimize the pH of the lysed cell solution and 2,2'-Azino-bis(3-ethylbenzo-thiazoline-6-sulfonic acid diammonium salt in an amount selected to react with myeloperoxidase.

16. The method according to claim 14 further including the step of pre-rinsing with a cleansing solution five seconds to five minutes prior to obtaining said oral rinse sample.

17. The method as claimed in claim 15 wherein a colour intensity correlating to a number of said human neutrophils greater than 5,000,000 is indicative of a moderate onset of periodontal disease.

18. The method as claimed in claim 14 wherein said colourimetric reagent further comprises hydrogen peroxide and a neutrophil-reactant salt comprising an ABTS (2,2'-Azino-bis (3-ethylbenzo-thiazoline-6-Sulfonic acid) diammonium salt in an effective amount selected to react with said neutrophils so as to form a colour indicator.

* * * * *